United States Patent
Salzmann

[11] Patent Number: 5,906,939
[45] Date of Patent: May 25, 1999

[54] CULTURED FIBROBLAST OR EPITHELIAL CELL DISSOCIATION METHOD USING SULFATED POLYSACCHARIDE AND CHELATOR

[75] Inventor: Jean-Loup Salzmann, Paris, France

[73] Assignee: Universite Pierre Et Marie Curie (Paris VI), Paris, France

[21] Appl. No.: 08/836,596

[22] PCT Filed: Oct. 31, 1995

[86] PCT No.: PCT/FR95/01435

§ 371 Date: May 2, 1997

§ 102(e) Date: May 2, 1997

[87] PCT Pub. No.: WO96/14395

PCT Pub. Date: May 17, 1996

[30] Foreign Application Priority Data

Nov. 4, 1994 [FR] France ................................ 94 13249

[51] Int. Cl.[6] ........................................................ C12N 5/00
[52] U.S. Cl. ................................................................ 435/378
[58] Field of Search ................................................ 435/378

[56] References Cited

U.S. PATENT DOCUMENTS 5,348,877  9/1994  McKenna et al. .
5,554,527  9/1996  Fickenscher ....................... 435/240.1

FOREIGN PATENT DOCUMENTS 0 142 344   2/1985  European Pat. Off. .
WO 89/01028  2/1989  WIPO .

OTHER PUBLICATIONS

Thurn et al., "Heparin–induced aggregation of lymphoid cells", J. Cell. Physiol. 126 (3) : 352–8 (1986).
Clarke et al., "Attachment of fibroblasts to a polyanionic surface", Exp. Cell Res. 102 (2) :441–5 (1976).
Klebe et al., "Effect of glycosaminoglycans on fibronectin––mediated cell attachment" J. Cell. Physiol. 112 (1) : 5–9 (1982).
San Antonio et al, "Heparin Inhibits the Attachment and Growth of Balb/c–3T3 Fibroblasts on Collagen Substrata", Journal of Cellular Physiology 150(1):8–16 (1992).

*Primary Examiner*—Sandra E. Saucier
*Attorney, Agent, or Firm*—Nixon & Vanderhye P.C.

[57] ABSTRACT

A cultured eukaryotic cell dissociation method using at least one polysaccharide polymer derivative. In particular, the method of dissociating cultured, adherent fibroblast or epithelial cells using a chelating agent such as EDTA and a sulfated polysaccharide such as heparin is disclosed.

6 Claims, No Drawings

CULTURED FIBROBLAST OR EPITHELIAL CELL DISSOCIATION METHOD USING SULFATED POLYSACCHARIDE AND CHELATOR

The present invention relates to an improvement of the methods of collection and manipulation of adherent eukaryotic cells or of cultured tissues.

Cell culture is currently one of the unavoidable procedures entailed in genetic engineering techniques, either for expressing recombinant proteins or, when these cells have been transfected by recombinant viruses, as host cells which can be administered in gene therapy. In the latter case, cells transfected by viral or retroviral vectors are in some cases reimplanted directly in tissues: a review of these different techniques is given in the work entitled "Thérapie génique, l'ADN médicaments" coordinated by Axel Kahn, publisher John Libby, (1993); reference may usefully be made also to the paper by R. C. Mulligan, Science (1993), Vol.: 260, p 926.

The yield of viable cells is a critical factor when eukaryotic cells are cultured, both as regards the actual quality of the cells or of the products which are obtained therefrom, and as regards the questions of yield which influence both the amounts of products obtained and the production cost of the said product; in particular when a gene therapy procedure is carried out by injection of cells, for example packaging cells, containing a recombinant virus or retrovirus, the infectious titre of the virus or retrovirus depending directly on the physiological state of the packaging cells and on their concentration.

Adherent cells are often used in cell culture for the production of products which are either secreted by these cells or as such in gene therapy; the most classical examples are either CHO cells (Chinese hamster ovary cells) for the production of recombinant molecules or cloned receptors, or other, fibroblast cells used in gene therapy, and especially cells derived from 3T3 such as NIH-3T3.

In order to detach the cells from their support, various physical techniques (scraper) or chemical techniques (chelators of the EDTA type or proteolytic enzymes of the trypsin type) have been employed. All these techniques have some drawbacks.

The use of physical means or of chelators such as EDTA is intricate and gives rise to the appearance of aggregate as well as a decrease in viability; proteolytic enzymes such as trypsin degrade the cell surface proteins, decrease viability and interfere with their biological property without even completely eliminating the presence of aggregates, leading to lower degrees of infectivity than could be the case; the cells no longer have available to them the surface glycoproteins enabling them to produce retroviruses at an optimum titre.

This applies, for example, to the use of NIH-3T3 packaging cells, which are mouse fibroblasts used in gene therapy, and are cultured on plastic supports and then collected and injected directly into tumours; the principle of this type of therapy is to make particular derivatives of NIH-3T3 cells, known as M11 cells, produce therapeutic retroviruses in vivo within the tumours; as an example of such a treatment, reference may be made to the papers by M. Caruso et al. in Proc. Nat. Acad. Sci. USA, (1993) 90: 7024–7028; or K. W. Culver et al., Science 256 No. 5063 pp. 1550–1551 (1992). The integrity and capacity of these cells to produce viruses are hence fundamental to the therapeutic efficacy of the treatment.

Aggregates have a whole series of drawbacks, the biggest of which are that they give rise to an underestimate of the number of cells and very poor reproducibility of the cell counts. Furthermore, the presence of aggregates interferes with the freezing processes which are essential to good storage of the cells, the cells situated in the middle of the aggregates not being reached by the preservation products such as dimethyl sulphoxide (DMSO), thereby making them more fragile and giving rise to greater mortality. Lastly, aggregates interfere with the diffusion of the cells when they are injected into tissues or tumours in the course of gene therapy treatments.

The devices permitting bulk cell culture of adherent eukaryotic cells are of various types, the principle always being to have a maximum surface area enabling the cells to adhere to this surface; the following may be mentioned by way of example and since they are the commonest devices:
- roller bottles in which the cells coat a cylindrical wall of the bottles,
- so-called "multi-tray" apparatuses, consisting of a series of superposed plates to which the cells attach themselves and bathing in the culture medium, or alternatively apparatuses of the CellCube type,
- microcarriers or microbeads such as the ones marketed by the company Pharmacia under the brand names Cytodex 1, 2 or 3 or alternatively Cytopore,
- various existing systems containing, as an example, cartridges of hollow fibers in which the cells are accommodated, among which systems those of the Cellmax or Endotronix type may be mentioned.

When it is desired to recover cells for any reason, in particular in order to build up cell banks, to culture them again or alternatively to use them as therapeutic agents, the succession of steps is as follows:
a) culture of the cells or tissues in nutrient medium,
b) removal of the cell culture medium,
c) addition of a dissociation medium comprising a chelator or a proteolytic enzyme or a combination of both,
d) one or more steps of washing in a medium suited to the use which it is desired to make of these cells.

If these cells are intended for freezing, they are taken up in a medium containing from 5 to 20% of DMSO and from 30 to 70% of foetal calf serum; the frozen cells are then thawed by resuspension in a medium composed of physiological saline to which 10% albumin is added, and the cells are then washed and centrifuged several times in the same medium until the cell pellet is taken up in the final medium suited to their use.

The problem of preservation of these cells in the isolated state, while having their membrane integrity and retaining maximum viability, is a problem which has not been solved at the present time. The invention solves this problem by affording a method of preparation of adherent eukaryotic cells, comprising at least one of the steps mentioned above, including that of culture itself, and consisting in adding a derivative of a polyglycosidic polymer to a solution in contact with the cells during one of these steps. Preferably, this polyglycosidic polymer is a polysaccharide, and preferably a sulphated polysaccharide; examples of such sulphated polysaccharides are, for example, heparin, dextran sulphate and hydroxyethylstarch sulphate. A polysaccharide according to the invention to be added to the solutions for treatment of eukaryotic cells has a molecular weight preferably of between 5000 and 500,000. Heparin of molecular weight 20,000 constitutes a special case which is especially effective in the method of the invention. Heparin is currently known and used as an anticoagulant. Several medicinal products based on heparin or on heparin derivatives have received an authorization for placing on the market for this indication.

However, the advantage of adding heparin in the method of the invention cannot be explained by a physiological mechanism such as the one involved in coagulation or haemostasis.

The dose of sulphated polysaccharides to be added in the method of the invention is from 50 to 500 units per ml, and preferably from 75 to 150 units per ml, when the medium is a dissociation solution containing a chelator or an enzyme (Steps b) to d)). This dose is from 500 to 5000 IU/ml when the polysaccharide is added directly to the culture medium of the cells or tissues (step a)), and preferably 800 to 2000 IU/ml; a concentration of approximately 1600 IU/ml may be considered to be optimal.

This effect of sulphated polysaccharides on the prevention of the aggregation of adherent cells cannot be explained either by its known anti-aggregating properties, or by its well-known action of inhibition of the conversion of prothrombin to thrombin. In fact, the action of heparin on the capacities of adhesion of cells to their support is still poorly understood and the few published results are contradictory. Sometimes the addition of heparin to the culture medium gives rise to an increased aggregation of the cells (Heparin induced aggregation of lymphoid cells: J. Cell. Physiol 1986, 126, 352–358), sometimes heparin gives rise to a detachment of the cells or an inhibition of their attachment to artificial substrates (Heparin inhibits the attachment and growth of BALB/C/3T3 fibroblasts on collagen substrata, J. Cellular Physiol. 1992, 150, 8–16).

The invention also relates to the use of a polyglycosidic polymer derivative, in particular of sulphated polysaccharides, in the culture medium, in a dissociation medium and also in the freezing or thawing media of adherent eukaryotic cells or of tissues in culture. Heparin, dextran sulphate or hydroxyethylstarch sulphate are preferred sulphated polysaccharides of the invention. This use makes it possible:

- to obtain better dissociation of the cells,
- to obtain these cells with a yield higher than that obtained by the traditional methods,
- to decrease the size and number of the aggregates which persist after the dissociation step,
- to obtain better reproducibility in the cell counts,
- to optimize the procedures of freezing or thawing and of injection (when this is their final use) of these cells.

When the polymer derivative is used in the dissociation medium of the cells or tissues and containing either a chelator or a proteolytic enzyme or both, the optimum dose is between 75 and 150 IU/ml. When the polymer derivative is used directly in the culture medium, its optimum concentration is between 500 and 5000 IU/ml, and preferably between 800 and 2000 IU/ml, with an optimum concentration around 1600 IU/ml. The advantage of the latter situation lies, on the one hand in the increase in cell viability which it makes possible, and on the other hand in the economy of means for arriving at the harvesting of the cells in culture or the tissues while avoiding the dissociation step; in effect, a simple centrifugation step, where appropriate followed by a washing step, is sufficient for obtaining a cell pellet which is ready for possible freezing.

The invention also relates to the eukaryotic cells obtained by carrying Out a method as described above, as well as to the products originating from these cells or tissues, in particular viruses, recombinant proteins or receptors.

Particular examples of this type of cell are, in particular: L cells, the NIH-3T3 line, the ΨCRE and ΨCRIP encapsidation lines, TS13 cells (hamster cells), MC26 tumour cells, 143b tumour cells, MDF7 tumour cells, B16 F1 tumour cells, GP+envAM12 packaging lines and HeLa cells. An example of tissue in culture is that of keratinocyte monolayers.

The use of recombinant eukaryotic cells or cells transformed for use in gene therapy is currently assuming increasing importance, and the same applies to the volumes to be produced. The method of the invention is considerably improved when, after the first step of dissociation of the cells, the remainder of the treatment process, suspension, resuspension and washes, is performed at a temperature of 4° C. instead of being performed at room temperature. Thus, the process as described above is especially advantageous when all of these intermediate steps are carried out at 4° C.

Since the use of these cell types is essentially for therapeutic purposes in man, it is advantageous to stress that the sulphated polysaccharides such as the ones mentioned above are products which have already obtained an authorization for placing on the market and, as such, do not in principle create any problem of toxicity if potential residues remain attached to the cells.

In the embodiment of the method of the present invention in which the addition of heparin lies between 500 and 5000 IU/ml in the culture medium, and preferably between 800 and 2000 IU/ml, when the cells reach confluence, the cells are dissociated without performing the steps of removal of the culture medium or addition of dissociating medium containing, in particular, a chelator of the EDTA type. An advantage of this particular embodiment is the increase in cell viability; in effect, EDTA, which gives rise to a certain cell mortality, is no longer necessary. In this embodiment, the heparin added directly to the culture medium is left in contact with the cells for 5 to 10 minutes; the cells can then be readily dissociated by moderate agitation followed by resuspension, for example, with a pipette, and may thereafter be collected. Step d) mentioned above, of washing in a medium suited to the use which it is desired to make of these cells, is still possible subsequently.

This type of use makes it possible to improve greatly the methods used for collecting cells in roller bottles when the number of bottles to be recovered is large. This gives rise, in particular, to an economy of manipulations which makes it possible to render viable an industrial process which would otherwise not have been viable. By way of example, to collect the cells from 20 roller bottles according to a traditional dissociation method, it is necessary to use 6 people who work in a small space for a period of 2 to 3 hours. With the new method, 2 people suffice, without an increase in the time required. This improvement is hugely significant when the scale rises to 100 roller bottles, when the method of dissociation with a change of media becomes virtually impossible on account of the excessively large number of people present in a room with a controlled atmosphere. Lastly, the increase in cell viability in the absence of EDTA increases the quality and amount of the product obtained from the dissociated cells or tissues.

The experiments below are examples, given as a guide, of the improvement brought about by the method of the invention in the quality and yield of the cells obtained, as well as the improvement in the infectious titre of the cells derived from mouse fibroblasts transfected by recombinant retroviruses, such as ΨCRIP packing cells (Danos O. et al., Proc Natl Acad Sci U.S.A. 85: 64, 60-64-64 (1988)). These experiments are intended to illustrate the performance features of the method of the invention without, however, being limited either to the cell types given, or to the culture method used, or to the media, buffers or treatment of the cells used starting from the dissociation step.

All the examples below are carried out using heparin as marketed by the company Choay (Sanofi Winthrop, 9, rue du Président Allend, 94958 Gentilly Cedex) as sulphated polysaccharides, the lyophilized heparin being redissolved in sterile distilled water in the proportion of 25,000 units per ml.

The cells used are cells of the fibroblast type derived from NIH-3T3, transfected by a recombinant retrovirus of the Moloney type integrating in its genome a thymidine kinase gene and described in Caruso et al. 1993 Proc Natl Acad Sci USA 90: 7024–7028, and known as M11.

EXAMPLE NO. 1: EFFECT OF ADDING HEPARIN ON THE NUMBER OF CELLS DISSOCIATED AND COLLECTED

Cell growth is pursued to confluence in roller bottles up to the 6th or 8th day (D6 or D8) of production, the culture medium is then discarded and the cells are placed in contact with a dissociation medium consisting of PBS buffer to which 0.02% of EDTA is added. The cells are then counted in a Coulter counter on D6 or D8, either without the addition of heparin or with the addition of 100 units per ml of heparin; the results are presented in Table 1 below:

TABLE 1

| Number of cells harvested per roller bottle | | |
|---|---|---|
| HEPARIN | 0 | 100 U/ml |
| D6 | $124.10^6$ | $150.10^6$ |
| D8 | $136.10^6$ | $164.10^6$ |

It is seen that the number of cells harvested per roller bottle is 20% larger when 100 units per ml of heparin are added to the PBS-EDTA medium.

In addition, when the cell pellets are taken up in freezing medium, the number of aggregates re-formed is much smaller than in the absence of heparin.

EXAMPLE NO. 2: FREEZING, THEN THAWING OF CELLS IN THE ABSENCE OR PRESENCE OF HEPARIN 75-cm$^2$ culture dishes contain a lawn of M11 cells at confluence.

The cells are detached from the dish with PBS-0.02% EDTA dissociation medium with or without heparin at a concentration of 100 units per ml.

The dissociation medium is brought into contact with the cell lawn for 5 minutes, the cells are then recovered and dissociation is completed with a 5-ml pipette. The cells are then counted and centrifuged, and the cell pellet is taken up in a suitable volume of freezing medium composed of 50% of new-born calf serum (Hyclone reference A-2111) and 50% of DME medium containing 20% of DMSO. The DME medium is DMEM medium (Gibco reference 41965) to which 6 ml of glutamine, 6 ml of antibiotic solution (penicillin, streptomycin, neomycin (Gibco reference 15640-048)) and 10% of new-born calf serum are added. The cells are finally frozen in 50% new-born calf serum and 10% DMSO in DME.

Thawing Protocol

The ampoules containing the cells frozen in the medium described above are taken out of liquid nitrogen and placed in ice, and they are then transferred to a water bath at 37° C. until the first sign of separating ice is seen, the opportune moment for transfer to a 15-ml Falcon tube containing 10 ml of medium consisting of physiological saline to which 10% of human albumin is added. The cells are thereafter washed two or three times with this same medium, the cell pellet is then resuspended in an appropriate volume of DME (as defined above) containing 10% of new-born calf serum and the cell suspension is then distributed again in culture bottles, culturing being carried out under standard conditions at 37° C. in the presence of 5% of $CO_2$.

Table 2 below summarizes the results obtained under the following experimental conditions: during their growth after thawing, the DMEM culture medium contains from 0 to 100 units per ml of heparin, and the cells are then harvested in PBS-EDTA buffers with or without 100 units of heparin.

The parameters measured are the number of living cells, the viability, the cell density in the bottles, the doubling time and the number of doublings.

TABLE 2

| No. of IU of heparin in 30 ml of DMEM | 0 | | 25 U/ml | | | 50 U/ml | | | 75 U/ml | | 100 U/ml | |
|---|---|---|---|---|---|---|---|---|---|---|---|---|
| No. of IU of heparin in 10 ml of PBS-EDTA | 1000 | 0 | 1000 | 1000 | 0 | 0 | 1000 | 1000 | 0 | 0 | 1000 | 0 | 000 | 0 |
| No. of living cells (× $10^6$) | 3.2 | 2.1 | 2.33 | 2.36 | 2.48 | 1.74 | 1.96 | 2.64 | 1.44 | 2.48 | 1.98 | 1.32 | 1.6 | 1.03 |
| Viability | 90% | 72% | 91% | 86% | 86% | 75% | 87% | 92% | 89% | 91% | 83% | 80% | 83% | 82% |
| No. of living cells per cm$^2$ | 0.042 | 0.028 | 0.031 | 0.032 | 0.033 | 0.023 | 0.026 | 0.035 | 0.019 | 0.019 | 0.026 | 0.018 | 0.021 | 0.014 |
| Doubling time | 66h | 6d | 4.7d | 4.5d | 4.1d | 14d | 7.8d | 3.7d | — | 4.1d | 7.5d | — | — | — |
| Number of doublings | 1.09 | 0.46 | 0.63 | 0.65 | 0.72 | 0.21 | 0.38 | 0.81 | — | 0.72 | 0.4 | — | — | — |
| Confluence | 2+(+) | 2+(+) | 2+(+) | 2+(+) | 2+(+) | 2+(+) | 2+ | 2+ | 2+ | 2+ | 2+ | 2+ | 2+ | 2+ |

It is clearly apparent that the presence of heparin in the growth medium is seen to be unfavourable to the number of living cells obtained after harvesting.

In contrast, the presence of heparin in the detachment medium very significantly increases the number of living cells, the viability and the cell density.

On microscopic observation of the cells on D3, it is apparent that the number of cells in suspension increases with the heparin concentration in the medium and, conversely, the cell lawn is less dense.

The cells cultured in the presence of heparin and then treated in PBS and EDTA without heparin display a phenomenon of detachment of the cell lawn which falsifies the cell counts obtained from the detached lawn and decreases, in fact, the yield of the cells obtained.

This example shows clearly that the presence of heparin in the PBS-EDTA medium and in the freezing and thawing media endows the cells with a degree of viability of 90% and a yield of living cells which is much greater than that obtained in the absence of heparin.

EXAMPLE NO. 3: INFECTIOUS TITRE OF CELLS IN CULTURE WHICH HAVE BEEN IN CONTACT WITH HEPARIN FOR THE VARIOUS PHASES OF HARVESTING, FREEZING AND THAWING AS ARE DESCRIBED IN THE EXAMPLES ABOVE

Calculation of the infectious titre was carried out according to the method described in Caruso et al., Proc Nat Acad Sci (1992) 89: 182–186. L cells in culture were infected with the M11 lines harvested in the manner described in the examples above. The L cells infected with the M11 cells are then stained with trypan blue.

The measurement of the infectious titre of these cells is identical to or greater than that obtained in simple PBS-EDTA medium, and consistently greater if the titre is referred to the number of cells actually counted; it is also significantly greater than the titre of cells harvested with trypsin. In addition, with the use of trypsin, the infectious titre is invariably zero up to fourth hour whereas, in the presence of PBS and EDTA to which 100 units per ml of heparin are added, an infectious titre is apparent as early as the first hour after bringing the L cells into contact with the M11 cells.

These results clearly reflect the fact that M11 cells are in a better physiological state when the cells have been brought into contact with heparin beforehand during the steps of collection, freezing and thawing than when they have been only in the presence of EDTA or trypsin or a mixture of both.

EXAMPLE NO. 4: COMPARISON OF THE EFFECT OF LOW AND HIGH CONCENTRATIONS OF HEPARIN ON THE DISSOCIATION OF DIFFERENT CELL LINES IN CULTURE

The use of heparin was tested in relation to the dissociation of different cell lines. There may be mentioned the NIH-3T3 line, the ΨCRE and ΨCRIP encapsidation lines, TS13 cells (hamster cells), MC26 tumour cells, 143b tumour cells, MCF7 tumour cells, B16 F1 tumour cells, GP+envAM12 packaging lines and HeLa cells.

a) Heparin concentration at 100 IU/ml in PBS-EDTA medium at pH8:
The dissociation time for the heparin concentration at 100 IU/ml is 5 minutes at room temperature. These cells dissociate more readily as they approach confluence. If the heparin concentration is increased to approximately 200 IU/ml viability is slightly increased; it is 87%, whereas at 100 IU/ml it was 83%.

b) Heparin used at a concentration of between 800 IU/ml and 2000 IU/ml:
The heparin is added directly to the cell culture medium at a concentration of 1200 IU/ml; cell viability after dissociation is then 95%.

EXAMPLE NO. 5: USE OF HEPARIN FOR THE DISSOCIATION OF CELLS IN CULTURE IN SERUM-FREE MEDIUM

The experiment was carried out using MDCK type cells, which have to grow in a serum-free medium in order to be able to produce appreciable amounts of influenza virus after a suitable treatment. Unfortunately, this type of cell line cultured without serum makes it extremely difficult to dissociate the cells. The usual procedure is a treatment with a PBS-EDTA buffer for 30 minutes, followed by a very vigorous dissociation with trypsin. This difficulty in dissociating the cells is a considerable obstacle to the industrial use of this type of cell culture, which is, however, essential to the manufacture of influenza vaccine. With the method of the invention, the step of preincubation with PBS-EDTA has been replaced by the addition of heparin at high dose (1200 IU/ml) to the culture medium. In the majority of cases, a very considerable increase was observed in the subsequent dissociation in the presence of trypsin and, in some cases, it was possible to dissociate the cells without adding trypsin.

EXAMPLE NO. 6: DETACHMENT OF EPITHELIAL CELL MONOLAYERS

Reconstitution of the epidermis of third-degree burns victims is obtained by in-vitro culture of keratinocytes, which arrange themselves in monocellular layers on the culture dishes. The procedure normally used to recover these monolayers is a vigorous digestion with trypsin followed by physical detachment. The use of heparin advantageously replaces the use of trypsin, on the one hand because heparin is less damaging to the proteins at the surface of these cells, and on the other hand heparin is much cheaper and is suitable for use in man (an authorization for placing on the market exists) whereas trypsin, in order to be able to be used, has to require a large number of bacterial and viral controls which make it an extremely expensive product.

In conclusion, the addition of an amount of sulphated polysaccharides such as heparin at a concentration of 50 to 500 units per ml, and preferably around one hundred units per ml, to the media used for manipulation of adherent cells during their collection, freezing or thawing, or of an amount from 500 to 5,000 IU/ml to the culture medium, enables the viability and the absolute number of living cells obtained to be increased; concomitantly, a decrease in aggregates and a more vigorous physiological behaviour of the cells are observed, since an increase is observed in the infectivity of the cells transformed by a retrovirus.

Lastly, these experimental conditions enable the cell collection operations to be carried out at a temperature of 4°, which makes it possible to envisage a homogeneous treatment of a large amount of cells, this being necessary for the preparation of therapeutic batches.

It is especially interesting to note that the use of substances such as heparin or hydroxyethylstarch have already received authorizations for placing on the market for therapeutic uses, and in particular as an anti-aggregating agent in the case of the former or as a plasma substitute in the case of the latter, which suggests that the use of media containing them would not create any major problem in respect of the compilation of a clinical registration dossier for new therapeutic products based either on the cells in the case of gene therapy or on substances excreted by the cell in the case of recombinant proteins.

I claim:

1. A method of dissociating an adherent layer of cultured fibroblasts or epithelial cells from a surface comprising contacting said fibroblasts or epithelial cells with a sulfated polysaccharide having a molecular weight between 5000 and 500,000, and a chelating agent, in a concentration and for a time sufficient to effect said dissociation, and collecting the dissociated cells.

2. The method according to claim 1, wherein the polysaccharide is selected from the group consisting of heparin, dextran sulphate and hydroxyethylstarch sulphate.

3. The method according to claim 2, wherein the polysaccharide is heparin.

4. The method according to claim 1 wherein the cells are in a culture medium and the polysaccharide is present in the medium at a concentration of between 500 and 5000 IU/ml.

5. The method according to claim 1 wherein the cells are recombinant cells that produce a recombinant protein.

6. The method according to claim 1, wherein the cells are host cells comprising a recombinant retrovirus.

\* \* \* \* \*

UNITED STATES PATENT AND TRADEMARK OFFICE
CERTIFICATE OF CORRECTION

PATENT NO.    : 5,906,939
DATED         : May 25, 1999
INVENTOR(S)   : Salzmann

It is certified that error appears in the above-identified patent and that said Letters Patent is hereby corrected as shown below:

Column 6,
Table 2, penultimate row, column 3, change "0.46" to -- 0.48 --.

Signed and Sealed this

Twenty-second Day of October, 2002

Attest:

Attesting Officer

JAMES E. ROGAN
Director of the United States Patent and Trademark Office